US009408404B2

(12) United States Patent
Weaver et al.

(10) Patent No.: US 9,408,404 B2
(45) Date of Patent: *Aug. 9, 2016

(54) METHOD FOR PRODUCING LIPIDS BY LIBERATION FROM BIOMASS

(75) Inventors: Craig A. Weaver, Boulder, CO (US); Joseph M. Kobzeff, Charlottesville, VA (US); Paul W. Behrens, Ellicot City, MD (US); Jaouad Fichtali, Lexington, KY (US); Rebecca M. Bell, Crownsville, MD (US)

(73) Assignee: DSM IP Assets B.V., TE Heerlen (NL)

( * ) Notice: Subject to any disclaimer, the term of this patent is extended or adjusted under 35 U.S.C. 154(b) by 1849 days.

This patent is subject to a terminal disclaimer.

(21) Appl. No.: 10/971,723

(22) Filed: Oct. 22, 2004

(65) Prior Publication Data

US 2005/0170479 A1     Aug. 4, 2005

Related U.S. Application Data

(63) Continuation-in-part of application No. PCT/US03/14177, filed on May 5, 2003.

(60) Provisional application No. 60/377,550, filed on May 3, 2002.

(51) Int. Cl.
| | |
|---|---|
| *A23D 9/00* | (2006.01) |
| *A23L 1/29* | (2006.01) |
| *A23L 1/30* | (2006.01) |
| *C11B 1/02* | (2006.01) |
| *C11B 3/00* | (2006.01) |
| *C11B 5/00* | (2006.01) |
| *C12N 1/06* | (2006.01) |
| *C12P 7/64* | (2006.01) |
| *A61K 31/202* | (2006.01) |

(52) U.S. Cl.
CPC . *A23D 9/00* (2013.01); *A23L 1/296* (2013.01); *A23L 1/3006* (2013.01); *A23L 1/3008* (2013.01); *A61K 31/202* (2013.01); *C11B 1/025* (2013.01); *C11B 3/001* (2013.01); *C11B 5/0021* (2013.01); *C12N 1/06* (2013.01); *C12N 1/066* (2013.01); *C12P 7/6472* (2013.01); *A23V 2002/00* (2013.01)

(58) Field of Classification Search
CPC .................. A23V 2002/00; A23V 2250/1882; A23V 2200/32; A23V 2200/324; A23V 2250/18; C11B 1/025; C11B 3/001; C11B 1/10; C11B 3/10; C11B 5/0092; C11B 7/0075; C11B 1/02; C11B 5/00; C11B 5/0021; C11B 1/108; A23L 1/3008; A23L 1/3014; A23L 1/3053; A23L 1/293; A23L 1/296; A61K 2300/00; A61K 31/202; A61K 31/232; A61K 31/4709; A61K 31/517; A61K 47/12; A61K 31/20; A61K 31/201; A61K 47/44; A61K 36/02; A61K 36/06; A61K 47/10; A61K 47/42; A61K 9/48; A23K 1/164; A23K 1/003; A23K 1/007; A23D 9/00; A23D 7/00
See application file for complete search history.

(56) References Cited

U.S. PATENT DOCUMENTS

| | | | |
|---|---|---|---|
| 5,130,242 A | 7/1992 | Barclay | |
| 5,133,963 A | 7/1992 | Ise | |
| 5,288,619 A * | 2/1994 | Brown et al. | 435/134 |
| 5,340,742 A * | 8/1994 | Barclay | 435/256.8 |
| 5,969,169 A | 10/1999 | Fan | |
| 6,127,185 A | 10/2000 | Melton et al. | |
| 6,201,145 B1 | 3/2001 | Fan | |
| 6,204,401 B1 | 3/2001 | Perrut et al. | |
| 6,255,505 B1 | 7/2001 | Bijl et al. | |
| 6,270,828 B1 | 8/2001 | DeBonte et al. | |
| 6,541,049 B2 * | 4/2003 | Barclay | 426/7 |
| 2001/0046691 A1 * | 11/2001 | Bailey et al. | 435/134 |

FOREIGN PATENT DOCUMENTS

| | | |
|---|---|---|
| EP | 1 178 103 A1 | 2/2002 |
| EP | 1178118 A | 6/2002 |
| WO | WO9107498 | 5/1991 |
| WO | WO9737032 | 10/1997 |
| WO | WO0044862 | 8/2000 |
| WO | WO0210423 | 2/2002 |

OTHER PUBLICATIONS

Ellenbogen et al, "Polyunsat. Fatty Acids of Aquatic Fungi: Possilbe Phylogenetic Significance", Comp. Biochem. Physiol, 1968, vol. 29, pp. 805-811.*
International Search Report for PCT/US04/34965, date of mailing Sep. 26, 2007.
Opinion for PCT/US04/34965, date of mailing Sep. 26, 2007.
Macfarlane, et al., Inform, 2001 12:244-249.
International Search Report for International (PCT) Patent Application No. PCT/US03/14177, mailed Nov. 3, 2003.
Written Opinion for International (PCT) Patent Application No. PCT/US03/14177, mailed Jul. 1, 2004.
International Preliminary Examination Report for International (PCT) Patent Application No. PCT/US03/14177, mailed Feb. 17, 2005.
International Preiliminary Examination Report for International (PCT) Patent Application No. PCT/US2004/034965, mailed Dec. 27, 2007.

(Continued)

*Primary Examiner* — Debbie K Ware
(74) *Attorney, Agent, or Firm* — Shannon McGarrah; Xi Chen

(57) ABSTRACT

Disclosed are methods of preparing high-quality polyunsaturated fatty acid-containing lipids from a lipid-containing material that include enzymatic treatment of components of the material and/or pressure disruption of the material. Lipid-containing materials include biomass, such as microorganisms. The invention further includes products containing the lipid compositions, such as dietary supplements, food products, pharmaceutical formulations, humanized animal milk, and infant formula.

40 Claims, No Drawings

(56) References Cited

OTHER PUBLICATIONS

Communication in Cases for Which no Other Form is Applicable, including Corrected International Search Report and Corrected Written Opinion for International (PCT) Patent Application No. PCT/US2004/034965, mailed Oct. 31, 2007.
U.S. Appl. No. 11/828,636, filed Jul. 26, 2007, Kobzeff et al.
U.S. Appl. No. 11/828,635, filed Jul. 26, 2007, Kobzeff et al.
Extended European Search Report for European Patent Application No. 10 17 7024.6, European Patent Office, Munich, Germany mailed Nov. 24, 2010.
Office Action mailed Mar. 1, 2010, in U.S. Appl. No. 10/513,576, Kobzeff et al., with a 35 U.S.C. § 371(c) date of Oct. 11, 2005.
Office Action mailed Jun. 1, 2009, in U.S. Appl. No. 10/513,576, Kobzeff et al., with a 35 U.S.C. § 371(c) date of Oct. 11, 2005.
Office Action mailed Dec. 1, 2008, in U.S. Appl. No. 10/513,576, Kobzeff et al., with a 35 U.S.C. § 371(c) date of Oct. 11, 2005.
Office Action mailed May 14, 2008, in U.S. Appl. No. 10/513,576, Kobzeff et al., with a 35 U.S.C. § 371(c) date of Oct. 11, 2005.
Akoh, C.C. and D.B. Min, ed., *Food Lipids: Chemistry, Nutrition, and Biotechnology*, pp. 208-385, New York: Marcel Dekker, Inc., 1998.
Gunstone, F.D., John L. Hardwood, and Fred B. Padley, ed., *The Lipid Handbook*, pp. 258-261, London: Chapman & Hall, 1995.
Lin, C., et al., "Efficiency of Removing Volatiles from Menhaden Oils by Refining, Bleaching, and Deodorization," *J. Food Sci.* 55: 1669-1672, Institute of Food Technologists, United States (1990).
List, G., et al., "Oxidation and Quality of Soybean Oil: A Preliminary Study of the Anisidine Test," *J. Am. Oil Chem. Soc.* 51:17-21, American Oil Chemists Society, United States (1974).
Bailey et al., Bailey's Industrial Oil and Fat Products, Canola Oil: Physical and Chemical Properties, 1996, p. 53, N/A, John Wiley & Sons Inc., US.
Doisaki, N., Declaration of Nobushige Doisaki, N/A, 2012, N/A, N/A, US.
Gras Exemption Claim for Docosahexaenoic Acid Rich Oil Derived from Tuna (DHA-rich oil) and Arachidonic Acid Rich Oil Derived from Mortierella alpine Peyronel 1S-4 (M. alpine) (AA-rich oil; SUNTGA40S) as Sources of DHA and AA in Term and Preterm Infant Formulas dated Dec. 18, 2001.
Kyle et al., Industrial Applications of Single Cell Oils, n/a, 1992, n/a, n/a, US.
Myber et al., Stereospecific Analysis of Triacylglycerols Rich in Long-Chain Polyunsaturated Fatty Acids, Lipids, 1996, p. 207-215, 31(2), US.
Public Disclosure, Federal Register, 1997, n/a, 62(74), US.
Rosenthal et al., "Aqueous and enzymatic processes for edible oil extraction", Enzyme and Microbial Technology, vol. 19, pp. 402-420 (1996).
Seher, A., Sterols in the chemistry and technology of edible fats and oils, Lipids, 1976, N/A, 2, US.
Neete et al., Sterols and fatty acids of the Mortierellaceae: taxonomic implications, Mycologia, 1999, 642-649, 91 (4), US.

\* cited by examiner

METHOD FOR PRODUCING LIPIDS BY LIBERATION FROM BIOMASS

REFERENCE TO RELATED APPLICATIONS

This application is a continuation-in-part of and claims the benefit of priority under 35 U.S.C. 120 from prior pending PCT application PCT/US2003/014177, filed May 5, 2003, which in turn claims priority under 35 U.S.C. §119(e) from U.S. Provisional Application Ser. No. 60/377,550, filed May 3, 2002, all which are incorporated herein by reference in their entirety.

FIELD OF THE INVENTION

The present invention is directed to methods are provided for producing high-quality lipids that include the step of liberating lipids from biomass, such as algal biomass. The method includes using enzymatic treatment and/or a pressure disruption step.

BACKGROUND OF THE INVENTION

Various methods have been employed for extracting lipids from biomass. Techniques include direct extraction of the biomass with solvents, heating, pressure waves generated via electric arcs, direct saponification via KOH and ethanol, sonication, freezing and grinding and bead mills. For example, the biomass can be dried and the lipid extracted with a solvent such as hexane. Alternatively, a microbial fermentation broth can be subjected to extreme conditions of pH and/or temperature or additional equipment such as a homogenizer or pressure disruption device can be used to disrupt the cells. Some microbial biomasses such as *Crypthecodinium cohnii* have proven to be especially difficult to extract. Current methods to disrupt *Crypthecodinium* biomass include methods such as the one described in Triplett et al., Molecular Marine Biology and Biotechnology 2:239-245 (1993). Triplett uses glass beads to disrupt *Crypthecodinium* cells. Other methods include pressure disruption of a hexane-treated spray dried biomass, using high pressure drops of 12,000 to 20,000 psi to achieve satisfactory breakage of the cells.

Problems with prior methods include poor product quality due to chemically aggressive conditions of high temperature and high pH, high costs due to the need to spray dry the biomass or for additional equipment such as homogenizers and pressure vessels. Spray drying contributes considerably due to costs and the time required to spray dry. Furthermore, eliminating spray drying is advantageous because spray drying exposes the biomass to the high temperatures that are characteristic of a spray dryer. High temperatures may cause undesirable degradation and oxidation of the lipids. Use of prior methods of high pressure disruption necessitates frequent downtime to allow for maintenance of the cell breakage equipment. Even short periods of downtime are costly to the overall process.

The oxidative state of the lipid or lipid-containing material is strongly impacted by the processing conditions used to make the material. For food materials, the conditions during processing as well as the actual ingredients and quality of the ingredients will affect the oxidation state. For fermentation-derived lipids (e.g., lipids obtained from microbes grown in fermentors, ponds, etc.), the ingredients (fermentation and post-fermentation) used as well as the conditions during the lipid extraction and fermentation will affect the quality. Other sources of PUFAs, such as agricultural crops and animal sources, will also be affected by the processing conditions used to obtain the lipids and lipid-containing materials.

SUMMARY OF THE INVENTION

The present invention is directed to a method for obtaining a polyunsaturated fatty acid-containing lipid by providing a biomass comprising a polyunsaturated fatty acid-containing lipid, contacting the biomass with an enzyme and recovering lipid. Preferably, the method is conducted in the substantial absence of an extraction solvent, is conducted at a temperature of from about 10 C to about 80 C at a pH level of from about pH 5 to about pH 9, and/or is conducted from about 40 C to about 65 C. In preferred embodiments, wherein the biomass includes a marine microorganism selected from algae, bacteria, fungi and protests, and is preferably an algae. The biomass can include a microorganism from either the group of dinoflagellates and golden algae, and can include a microorganism from the genus *Thraustochytrium* (including *Ulkenia*), genus *Schizochytrium*, genus *Althornia*, genus *Aplanochytrium*, genus *Japonochytrium*, genus *Labyrinthula*, or genus *Labyrithuloides*. In preferred embodiments, the biomass can include the marine microorganism *Crypthecodinium cohnii*, the marine microorganism genus *Schizochytrium*, or the fungi *Mortierella alpina*. In various embodiments, the method can also include contacting the biomass with a surfactant.

The enzyme in the method can be selected from a lipase, a protease, a carbohydrase, a cellulase, a hemicellulase, a xylanthase, and combinations thereof. The step of contacting the biomass with an enzyme can include treating the biomass with an enzyme cocktail of a protease, a carbohydrase, and a cellulose.

In a further embodiment, the step of providing a biomass can include separating the lipid from a fermentation broth, and the separated lipid can be in the form of an emulsion. The emulsion can be treated by drying the emulsion or by treatment to release the lipid from the emulsion.

The method can also include treating the lipid by at least one additional treatment selected from treatment with a polar organic solvent, salt, precipitating agent, a second enzyme, heating, and cooling. The lipid can also be further treated by a treatment selected from drying, refining, bleaching, deodorizing, fractionating, winterizing, and interesterifying. The lipid can also be further treated by a treatment selected from the group consisting of treatment with antioxidants and metal ion capturing agents selected from the group consisting of chelating agents, ion exchange resins, and precipitating agents.

The method can further include pressure disruption of the biomass, such as by subjecting the biomass to a pressure differential of between about 2,000 psi and about 12,000 psi, a pressure differential of between about 4,000 psi and about 10,000 psi, a pressure differential of between about 5,000 psi and about 8,000 psi, or a pressure differential between about 6,000 psi and about 7,000 psi.

In preferred embodiments, the recovery of lipid from the biomass is greater than about 90% and preferably greater than about 95%. In preferred embodiments, at least a portion of the polyunsaturated lipid present in the lipid is a long chain polyunsaturated fatty acid, preferably having a carbon chain length of at least 20 or 22. The polyunsaturated lipid present in the lipid can have at least 3 or 4 double bonds. The polyunsaturated lipid can include at least about 10, 20, or 30 weight percent docosahexaenoic acid. The polyunsaturated lipid can include at least about 5, 10, 15, or 20 weight percent docosapentaenoic acid. The polyunsaturated lipid can include at least about 20, 30, 40, or 50 weight percent arachidonic acid. The lipid can include a monoacylglycerol, a diacylglycerol, or a triacylglycerol.

A further embodiment of the present invention includes a method for obtaining a polyunsaturated fatty acid-containing lipid by providing a biomass having such a lipid, contacting the biomass with an enzyme, disrupting cells in the biomass by pressure disruption, and recovering said lipid.

A further embodiment of the present invention includes a method for obtaining a polyunsaturated fatty acid-containing lipid by providing a biomass comprising a polyunsaturated fatty acid-containing lipid, disrupting cells in the biomass by pressure disruption by a pressure differential of less than about 12,000 psi, and recovering said lipid.

Also included are lipid compositions produced by the methods of the present invention.

DETAILED DESCRIPTION OF THE INVENTION

The present invention provides for an improvement in efficiency and ease of extraction of lipids and/or fats from a biomass. More specifically, the inventors have discovered that the efficiency of extraction can be improved by methods including enzyme treatment and/or pressure disruption.

In one embodiment, the present invention includes a method for obtaining a polyunsaturated fatty acid-containing lipid, which includes providing a biomass comprising a polyunsaturated fatty acid-containing lipid, contacting the biomass with an enzyme, and recovering the lipid.

A biomass useful in the present invention can be any source of a polyunsaturated fatty acid-containing lipid that is capable of liberation by enzymes and/or pressure disruption as in the present invention. Preferred polyunsaturated fatty acid-containing sources include animal, plant and/or microbial sources. Examples of animal sources include aquatic animals (e.g., fish, marine mammals, crustaceans, rotifers, etc.) and lipids extracted from animal tissues (e.g., brain, liver, eyes, etc.). Examples of plant sources include macroalgae, flaxseeds, rapeseeds, corn, evening primrose, soy and borage. Examples of microorganisms include algae, protists, bacteria and fungi (including yeast). The use of a microorganism source, such as algae, can provide organoleptic advantages, i.e., fatty acids from a microorganism source may not have the fishy taste and smell that fatty acids from a fish source tend to have.

Preferably, when microorganisms are the biomass, the microorganisms are cultured in a fermentation medium in a fermentor. Alternatively, the microorganisms can be cultured photosynthetically in a photobioreactor or pond. Preferably, the microorganisms are lipid-rich microorganisms, and more preferably, the microorganisms are selected from the group consisting of algae, bacteria, fungi and protists. Preferably, the microorganisms are selected from the group consisting of golden algae, green algae, dinoflagellates, yeast, and fungi. Preferably, the microorganisms are selected from microorganisms of the order Stramenopila or microorganisms of the order Thraustochytriales. Preferably, microorganisms are selected from the genus *Crypthecodinium, Mortierella, Thraustochytrium* (including *Ulkenia*), *Schizochytrium, Althornia, Aplanochytrium, Japonochytrium, Labyrinthula, Labyrithuloides* or mixtures thereof. Preferably, the microorganisms are selected from the group consisting of microorganisms having the identifying characteristics of ATCC number 20888, ATCC number 20889, ATCC number 20890, ATCC number 20891 and ATCC number 20892, strains of *Mortierella schmuckeri* and *Mortierella alpina*, strains of *Crypthecodinium cohnii*, mutant strains derived from any of the foregoing, and mixtures thereof. It should be noted that many experts agree that *Ulkenia* is not a separate genus from the genus *Thraustochytrium*. Accordingly, as used herein, the genus *Thraustochytrium* will include *Ulkenia*. Information regarding preferred microorganisms of the present invention can be found in U.S. Pat. Nos. 5,407,957; 5,130,242 and 5,340,594, which are incorporated herein by reference in their entirety.

As used herein, the term "lipid" includes phospholipids; free fatty acids; esters of fatty acids; triacylglycerols; diacylglycerols; monoacylglycerols; lysophospholipids; soaps; phosphatides; sterols and sterol esters; carotenoids; xanthophylls (e.g., oxycarotenoids); hydrocarbons; other lipids known to one of ordinary skill in the art and mixtures thereof. Lipids recovered by the present invention include lipids comprising a polyunsaturated fatty acid, more particularly, a long chain polyunsaturated fatty acid, and even more particularly, a polyunsaturated fatty acid present in said lipid having a carbon chain length of at least 20 or 22. Such polyunsaturated fatty acids present can have at least 3 or at least 4 double bonds. More particularly, the polyunsaturated fatty acid can include docosahexaenoic acid (at least 10, 20, 30 or 35 weight percent), docosapentaenoic acid (at least 5, 10, 15, or 20 weight percent), and/or arachidonic acid (at least 20, 30, 40 or 50 weight percent). Polyunsaturated fatty acids include free fatty acids and compounds comprising PUFA residues, including phospholipids; esters of fatty acids; triacylglycerols; diacylglycerols; monoacylglycerols; lysophospholipids; phosphatides; etc.

The step of contacting the biomass with an enzyme is useful to liberate lipids by, e.g., degradation of cell walls of the lipid-containing material. For different lipid-containing materials, different enzymes and reaction conditions can be employed. For these different materials, an important enzyme selection criterion is to select an enzyme that will attack and degrade a portion of the material (such as the proteins, polysaccharides, cell wall, cell outer membrane, peptidoglycan layer, lipid bilayer, cellulose, chitin, hemicellulose, lignin, lignin-related compounds, etc.) that is otherwise impeding recovery of the oil. In some embodiments, nonspecific protease enzymes such as trypsin, chymotrypsin, or the like are used to degrade protein components of the oil-containing materials and carbohydrase enzymes such as amylase can be used to degrade carbohydrate components of the oil-containing materials. Suitable enzymes include proteases, carbohydrases, cellulases, hemicellulases, pectinases, and xylanases, including complexes. Preferably, the process can be conducted with a combination of enzymes, also referred to as an enzyme cocktail. In another embodiment, a lipase can be included in the mixture. A lipase is an enzyme that hydrolyzes glycerides. Therefore, care needs to be taken to avoid unacceptable levels of degradation of glycerides in the lipid product. For example, a lipase will hydrolyze a triglyceride producing a free fatty acid and a diglyceride. Therefore, additional embodiments involve the use of small amounts of lipase or conditions under which the lipase is only active a small amount of the time. Such control of lipase activity could be controlled for example, by the use of temperature sensitive enzymes or the introduction of lipase inhibitors. Examples of suitable enzymes include the enzyme combinations known as CELUCLAST®, ALCALASE® and VISCOZYME® (available from Novozyme), BIOCELLULASE W®, BIOCELLULASE AZ®, BIOPECTINASE CCM®, BIOPROTEASE A® and BIOPECTINASE KK PLUS® (all available from Quest International). Even more preferred are cocktails including a cocktail including CELUCLAST®, ALCALASE® AND VISCOZYME® and a cocktail including BIOCELLULASE W®, BIOCELLULASE AZ®, BIOPECTINASE CCM®, BIOPROTEASE A® and BIOPECTINASE KK PLUS®. In a preferred embodiment, the lipids are effectively liberated from, for example, *Crypthecodinium* sp and/or *Schizochytrium* sp organisms by treating the cells with a protease enzyme or an enzyme cocktail including protease enzyme. It is surprising that this particular class of enzymes is effective for these organisms due to the relatively small amount of protein normally found in the cell wall of these organisms.

The selection of reaction conditions, including enzyme type, enzyme concentration, temperature, pH, water activity, other reagent concentration, reaction time, etc. will depend in part on the specific enzyme and material that the lipid is being liberated from. These conditions can be readily determined from information about the enzyme (and typically available from the supplier or in the literature), or determined by somebody skilled in the art. Typical temperatures range between about 10 C and about 80 C, between about 20 C and about 80 C, between about 30 C and about 70 C, and between about 40 C and about 65 C, although some special enzymes may be sufficiently active and stable for use outside of these ranges. Typical enzyme concentrations can be as low as 0.01% to several percent. The reaction rate is related to the enzyme concentration with higher concentrations allowing for shorter reaction times. In some situations, it may be possible to use an even lower concentration, such as when a particular enzyme is extremely active or stable or when very long reaction times may be practical. Suitable conditions of pH are between about pH 4 and about pH 9.

In a further embodiment of the present invention, the biomass is contacted with a surfactant in addition to the enzymes. The inventors have surprisingly found that the use of surfactants together with enzymatic treatment can allow for milder reaction conditions than with enzymes alone for liberation of the lipids. Surfactants can be added at approximately the same time as the enzyme. Alternatively, surfactant can be added before or after the enzyme. Suitable surfactants include, but are not limited to: phospholipid, lysophospholipid, monoglycerides, diglycerides, mixed glycerides, partial glycerides, soaps, fatty acids, salts of fatty acids, amines, antifoam, acids or salts of sulfonic acid, detergents, polysorbates (e.g., polyethylene sorbitan monooleate), aliphatic acids and esters, polar organic molecules, alcohols, sulfates and sulfonates, nitrogen-containing compounds (e.g. amines, amides, polyamides), phosphates (e.g. alkyl-alkylene diphosphate, tributyl phosphate), silicones (e.g. tri- and tetra-alkyl silanes, silicone polymer containing silica, dimethyl silicone polymers, methyl silicones), sulfides and thio derivatives, halogenated compounds, triacylglycerols, long chain fatty waxes (e.g. vegetable oils and waxes), mineral oils, sulfated derivative of triacylglycerols and mineral oils, bentonite, and monosodium phosphate mixed with boric acid and ethyl carbonate. In this embodiment, the lipid is preferably liberated from the biomass without using extreme conditions of temperature or pH and without using additional equipment such as a homogenizer or drying the biomass prior to lipid removal. For example, the enzymatic treatment can be conducted at temperatures below about 80 C, more preferably below about 70 C, and even more preferably, below about 65 C, and at pH conditions of approximately 5-9. Other methods for liberation of lipids that can be used, alone or in combination with enzymatic treatment, include treatment with detergents, osmotic shock, freezing/thaw cycling, autolysis, solvents, acids, bases and heat treatment.

In a particular embodiment, using proteolytic treatment of the lipid-containing material without a surfactant, the proteolytic treatment can be conducted at higher temperatures, sufficient to achieve desirable levels of lipid liberation. For example, in this embodiment, the enzymatic treatment is conducted at temperatures of at least about 30 C, more preferably at least about 40 C, and most preferably at least about 50 C. It should be recognized however, that at higher temperatures, degradation of lipids can occur. Therefore, a temperature must be selected such that adequate lipid liberation is achieved without unacceptable levels of lipid degradation.

The process of the present invention further includes recovering lipid after contacting the biomass with an enzyme. For example, the lipid can then be isolated from other materials by centrifugation of the mixture. In some cases, the lipid will be incorporated into an emulsion. For some such applications, the emulsion itself might be the final product and can be used "as is" or dried. For other applications, the emulsion is treated to release the lipid for recovery separately. Treatment to break the emulsion can include treatment with a polar organic solvent, salt, precipitating agent, another enzyme (protease or other kind), heating, cooling, etc. The lipid can then be dried, refined, bleached, deodorized fractionated, winterized interesterified and/or treated by other chemical, physical or biological treatments as needed. The lipid can also be treated with antioxidants and/or metal ion capturing agents (such as chelating agents, ion exchange resin, precipitating agents) at any point before, during or after the process.

In the instance of a process in which an emulsion is formed, the use of a protease enzyme can help break down emulsion-stabilizing proteins present, thereby aiding in the breaking of an emulsion. The successful use of a protease for lipid liberation when the biomass is microalgae is surprising because, microalgae tend to have a low protein content (~15-22% compared to ~55% for *E. coli*), and have very robust cellular structure due to the presence of silica and polysaccharides such as cellulose.

In some cases, after the lipids are liberated from the biomass, the lipids can be separated from the undesired materials (e.g., cellular debris), such as by centrifugation, or other appropriate methods. In other cases, an agent such as an alcohol or other polar organic solvent can be added to facilitate the separation of the liberated lipid from the undesired material. In still other cases, a solvent in which the lipid is soluble can be added and facilitate the separation of the liberated lipid from the undesired material, e.g., by solvent extraction. Techniques for separating the lipids from undesired materials can be found in U.S. Pat. No. 5,928,696, U.S. patent application Ser. No. 09/766,500, and PCT Application Numbers US01/12047 and US01/12049, all of which are incorporated herein by reference in their entirety.

In another embodiment of the present invention, the processes of the present invention are combined with oxidation-reducing techniques, including one or more of: exclusion of air (and oxygen) and other oxidizing agents, processing with mild conditions (moderate temperature, moderate pH, short processing times, etc.), exclusion of metal ions such as copper and iron, exclusion of previously oxidized lipids (even if subsequently purified), exclusion of oxidation precursors, and the presence of antioxidant compounds (such as tocopherols, tocotrienols, BHA, carnisol, carnosic acid, ascorbic acid, L-ascorbic acid esters (including L-ascorbyl palmitate, L-ascorbyl stearate, L-ascorbyl oleate), rosemary, etc. as well as esters or derivatives of these compounds), to obtain minimally oxidized lipids.

Another embodiment of the invention is a method for obtaining a polyunsaturated fatty acid containing lipid that includes disrupting cells in a biomass by pressure disruption. These methods can be conducted alone or in combination with methods involving enzyme treatment as described above. In the case of a combination of enzyme treatment and pressure description, higher quality and/or higher yield can be achieved than with pressure disruption or enzyme treatment alone. It is believed that pressure disruption of cells can facilitate the enzyme reaction by allowing more intimate contact between the enzyme and its substrate. It is also believed that enzyme treatment can facilitate pressure disruption by weakening the cell walls and allowing the use of less extreme (pressure or shear) conditions. The use of pressure disruption with the enzyme or enzyme-surfactant process can allow the use of conditions that are more chemically mild than would be possible without the pressure disruption. In other cases, this combined process can allow use of a lower pressure (and also lower cost) pressure disruption.

Pressure disruption generally refers to a technique where a cell slurry is expelled through a restricted orifice valve. Without being bound by theory, cell disruption is believed to be accomplished by one or more of the three following mechanisms: impingement on the valve, high liquid shear in the orifice, and sudden pressure drop upon discharge, causing an 'explosion' of the cell. A preferred type of pressure disruption is one that allows for the application of high pressure to a sample volume, and then forces the cell slurry through an orifice to return to normal atmospheric pressure. This type of pressure disruption may also be referred to as homogenization. A preferred type of homogenization device is a French pressure cell. Both batch and continuous flow type French pressure cells may be used, but a continuous flow is preferred for large volumes.

Pressure disruption can be conducted at pressures of up to 20,000 psi or more. However, at such high pressures, the equipment operation and maintenance costs can be significant. In a preferred embodiment, the pressure differential, or the pressure to which the sample is subjected to before ejection from the pressure cell, is less than about 12,000 psi. More preferably, the pressure differential is between about 2,000 psi and about 12,000 psi; more preferably, the pressure differential is between about 4,000 psi and about 10,000 psi; more preferably, the pressure differential is between about 5,000 psi and about 8,000 psi, more preferably, the pressure differential is between about 6,000 psi and about 7,000 psi; and most preferably, the pressure differential is about 6,000 psi.

In processes of the present invention in which a biomass is treated by both enzyme treatment and pressure disruption, the treatments can be performed in any order, including simultaneously. Preferably, however, the enzyme treatment step is performed prior to the pressure disruption step.

By use of the various methods described above, high recoveries of lipids from biomass can be achieved. For example, the recovery of lipid from biomass can be greater than about 80%, about 85%, about 90%, about 95% and about 97%.

In a embodiment of the present invention, the present invention includes a method for obtaining a polyunsaturated fatty acid-containing lipid, which includes the steps of providing a biomass comprising a polyunsaturated fatty-acid containing lipid, disrupting the biomass by pressure disruption with a pressure differential of between about 2,000 psi and about 12,000 psi, and recovering the lipid.

In accordance with a further embodiment of the present invention, the processes previously described can be employed on lipid-bearing material that has been dried prior to lipid removal. While the highest quality and lowest cost process would normally be expected from material that has not been dried, there are cases where it would be advantageous to dry the material either prior to or at some intermediate point during the process, prior to lipid separation. Use of the previously described processes with drying can provide a partial improvement in quality and/or cost over processes that include drying and do not include the present processes. Some examples of when this drying step would be appropriate are when the facility for lipid separation is located remote from the fermentation or other upstream facility, or when there are scheduling difficulties between the lipid separation facility and the upstream facility, or when the lipid-containing material must be stored prior to separating the lipid.

In one aspect of the present invention, the lipid is used in an endproduct selected from the group consisting of a dietary supplement, a food product, a pharmaceutical formulation, a humanized animal milk, and an infant formula. A pharmaceutical formulation can include, but is not limited to: an anti-inflammatory formulation, a chemotherapeutic agent, an active excipient, an osteoporosis drug, an anti-depressant, an anti-convulsant, an anti-*Helicobactor pylori* drug, a drug for treatment of neurodegenerative disease, a drug for treatment of degenerative liver disease, an antibiotic, and a cholesterol lowering formulation. In one aspect, the endproduct is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, schizophrenia, depression, weight maintenance and peroxisomal disorder. The following examples are provided for the purpose of illustration and are not intended to limit the scope of the present invention.

EXAMPLES

Example 1

This example demonstrates both the successful lysis of a *Schizochytrium* micro-organism with enzymes and the improvement of lysis with the inclusion of a surfactant, Polysorbate 80.

*Schizochytrium* sp. fermentation broth was diluted and buffered as follows: 25 ml of broth was combined with 65 ml DI water, then 10 ml of pH 6.0 buffer (1.0 M 2-[N-morpholino]ethanesulfonic acid) was added.

To different aliquots of this broth mixture different combinations of enzyme and surfactant were added. After the enzyme and surfactant additions, the samples were incubated at 45 C for 1.5 hr, and then examined by microscope for degree of lysis. The results are shown below in Table 1:

TABLE 1

| Enzyme* | Surfactant | Degree of lysis |
| --- | --- | --- |
| None | Polysorbate 80 | No lysis |
| VISCOZYME ® L | Polysorbate 80 | No lysis |
| ALCALASE ® 2.4 L FG, VISCOZYME ® L | Polysorbate 80 | Mostly lysed |
| ALCALASE ® 2.4 L FG | Polysorbate 80 | Virtually all lysed |
| VISCOZYME ® L | None | No lysis |
| ALCALASE ® 2.4 L FG | None | Mostly unlysed |

*The enzymes are both from Novozymes North America, Inc. of Franklinton, NC.

Example 2

This example demonstrates that different surfactants can be successfully used with enzyme treatments.

Schizochytrium sp. fermentation broth was diluted and buffered as in Example 1.

A commercial protease (ALCALASE® 2.4 L FG, available from Novozymes North America, Inc. of Franklinton, N.C.) and a commercial carbohydrase (VISCOZYME® L, available from Novozymes North America, Inc. of Franklinton, N.C.) were added to the diluted and buffered broth. This broth mixture was divided and different surfactants were added as follows:

1. Polysorbate 80
2. Sodium lauryl sulfate
3. Mono and diglycerides (Dimodan CO-K from Danisco of New Century, KA)

After the surfactant addition, each sample was heated in a hot water bath (75 C) for approx. 5 min. Each sample was then held overnight at room temperature with mixing on a Fisher Hematology/Chemistry Mixer. The samples were examined under a microscope for degree of lysis. The results are shown below in Table 2:

TABLE 2

| Surfactant | Degree of lysis |
|---|---|
| Polysorbate 80 | ~100% |
| Sodium lauryl sulfate | ~40-60% |
| Dimodan CO-K | ~100% |

In this case both Polysorbate 80 and mono and diglycerides (Dimodan) were successful, whereas sodium lauryl sulfate was less successful.

Example 3

This example demonstrates the successful lysis of Schizochytrium cells with enzymes, the isolation of the lipid that was present in the cells and the very high quality of the lipid (very low anisidine value).

Schizochytrium sp. fermentation broth was treated with antioxidants (ascorbyl palmitate and tocopherols) and drum dried. This dried biomass was then treated as follows:

Added to distilled water (51 g of biomass to 300 g water)

The pH was adjusted to the range of 6.9-7.3 with 2N $H_2SO_4$

The mixture was heated to 60 C in a water bath 1.5 ml of ALCALASE 2.4L FG was added The broth mixture was then purged with nitrogen to exclude oxygen and incubated at 60 C for 15 hours 120 ml of isopropanol (99.9%) was added with gentle mixing The broth-alcohol mixture was then centrifuged at 4000 RPM for 5 minutes The lipid phase (supernatant) was collected The collected lipid was tested for anisidine and peroxide value per AOCS (American Oil Chemists Society) methods Cd 8-53 and Cd 18-90.

A sample of the dried biomass was also hexane extracted by combining with hexane and ball milled in a Swedish tube extraction system. The lipid collected was tested for anisidine value and peroxide value as the other lipid sample. The test results of the lipid collected by the two methods are shown below in Table 3:

TABLE 3

| Sample | Peroxide Value | Anisidine Value |
|---|---|---|
| Enzyme, isopropanol method | <0.1 | 0.8 |
| Hexane extracted | <0.1 | 3.0 |

Example 4

This example demonstrates that treatment of Crypthecodinium sp. with enzyme followed by pressure disruption significantly increased the degree of breakage (measured by the amount of fat that has been liberated from the cell pellet into the supernatant) compared to enzyme treatment alone.

1 liter of Crypthecodinium sp. fermentation broth, at the end of a fermentation run, was harvested. A sample was removed for the determination of dry weight and the quantitation of oil by FAME analysis. FAME estimation of lipids is described in Morrison and Smith, A Preparation of Fatty Acid Methyl Esters and Dimethylacetals From Lipids with Boron Fluoride-Methanol, J.Lip. Res. Vol. 5, 1964, and also the American Oil Chemist's Society Official Methods. The fermentation broth was pasteurized. For each reaction condition noted in the table below, 50 ml of the fermentation broth was used. Replicates of each reaction condition were performed. The samples were spun down to collect the cell pellet. Buffer and enzyme (BIOCELLULASE W®, available from Quest) (or no enzyme control) were added to 20 ml and vortexed. The amount of enzyme added was equal to the dry weight of the cells and the samples were at pH 5. The samples were then allowed to react for one hour at 50 C. 20 ml of a 50/50 mixture of hexane:IPA was added to the sample, vortexed, and centrifuged. The samples were then subjected to pressure disruption in a French Pressure cell press device (Thermoelectron) at various pressures: 20,000 psi, 10,000 psi, 6,000 psi, and 4000 psi, or no pressure disruption. The supernatant and pellet were freeze dried, and the dry weight and FAMEs were determined as shown below in Table 4:

TABLE 4

| Treatment | enzyme | pressure | % fat remaining in pellet (FAME) |
|---|---|---|---|
| control | none | none | 95.8 |
| No enzyme control | none | 20,000 psi | 8 |
| No French Press control | BIOCELLULASE W | none | 85.3 |
| Enzyme, pressure | BIOCELLULASE W | 4,000 psi | 11.3 |
| Enzyme, pressure | BIOCELLULASE W | 6,000 psi | 9.7 |
| Enzyme, pressure | BIOCELLULASE W | 10,000 psi | 8.8 |
| Enzyme, pressure | BIOCELLULASE W | 20,000 psi | 5.1 |

Example 5

This example demonstrates that treatment of Crypthecodinium sp. with enzyme followed by pressure disruption significantly increased the degree of breakage (measured by the amount of fat that had been liberated from the cell pellet into the supernatant) compared to pressure treatment alone.

Samples were prepared and treated as described above for Example 4. The results are summarized below in Table 5:

TABLE 5

| Treatment | Enzyme | Pressure | % fat remaining in pellet (FAME) |
|---|---|---|---|
| control | None | none | 88.1 |
| Enzyme, pressure | BIOCELLULASE W | 4,000 psi | 19.6 |
| No Enzyme, pressure | None | 4,000 psi | 27.3 |
| Enzyme, pressure | BIOCELLULASE W | 6000 psi | 5.2 |
| No Enzyme, pressure | None | 6000 psi | 19.4 |
| Enzyme, pressure | BIOCELLULASE W | 10,000 psi | 3 |
| No Enzyme, pressure | None | 10,000 psi | 16.3 |

Example 6

The following Example describes treatment of *Crypthecodinium* sp. with varying amounts of enzyme at 6,000 psi. Samples were prepared and treated as described above for Example 4. The results are summarized below in Table 6:

TABLE 6

| Treatment | Pressure | Enzyme amount | % fat remaining in pellet |
|---|---|---|---|
| No enzyme, No pressure | none | none | 76.5 |
| Enzyme, No pressure | none | 100% | 53 |
| No Enzyme, pressure | 6,000 psi | none | 17 |
| Enzyme, pressure | 6,000 psi | 100% | 9.3 |
| Enzyme, pressure | 6,000 psi | 50% | 18 |
| Enzyme, pressure | 6,000 psi | 25% | 16.6 |
| Enzyme, pressure | 6,000 psi | 10% | 17.9 |

The results indicate that lowering the amount of enzyme from 100% to 50% approximately doubled the amount of fat in the pellet.

Example 7

In this Example, a number of different enzyme treatments were used with pressure disruption. The enzymes used were BIOCELLULASE W®; a cocktail including CELUCLAST®, ALCALASE® AND VISCOZYME® (all from Novozyme, Inc.); and a cocktail including BIOCELLULASE W®, BIOCELLULASE AZ®, BIOPECTINASE CCM®, BIOPROTEASE A® and BIOPECTINASE KK PLUS® (all from Quest, Inc.) Samples were prepared and treated as described above for Example 4. The results are summarized below in Table 7:

TABLE 7

| Treatment | Enzyme | Pressure | % fat remaining in pellet |
|---|---|---|---|
| control | | none | 81.2 |
| No Enzyme control | | 6000 psi | 13.7 |
| Enzyme treatment 1 | BIOCELLULASE W ® | 6000 psi | 10.7 |
| Enzyme treatment 2: Novozyme cocktail | CELUCLAST ®, ALCALASE ® AND VISCOZYME ® | 6000 psi | 10.2 |
| Enzyme treatment 3: Quest Cocktail | BIOCELLULASE W ®, BIOCELLULASE AZ ®, BIOPECTINASE CCM ®, BIOPROTEASE A ® and BIOPECTINASE KK PLUS ® | 6000 psi | 5.4 |

The results indicated that the enzyme cocktail made up of the Novozyme products CELUCLAST®, ALCALASE® AND VISCOZYME® was about as effective as the BIOCELLULASE W® enzyme, at liberating lipid from the cells while the enzyme cocktail made up of the Quest products BIOCELLULASE W®, BIOCELLULASE AZ®, BIOPECTINASE CCM®, BIOPROTEASE A® and BIOPECTINASE KK PLUS® was more effective than either of the other two enzyme treatments.

Example 8

In this Example, various amounts of the enzyme cocktail including BIOCELLULASE W®, BIOCELLULASE AZ®, BIOPECTINASE CCM®, BIOPROTEASE A® and BIOPECTINASE KK PLUS® (all from Quest, Inc.) were used on *Crypthecodinium* biomass in the manner described in Example 4, and subjected to 6000 psi pressure disruption. The amount of enzyme is expressed as weight of each enzyme making up the cocktail to the dry weight of the biomass. The results are summarized below in Table 8:

TABLE 8

| Treatment | Amount of enzyme | pH of reaction | Pressure | % fat remaining in pellet |
|---|---|---|---|---|
| control | None | | none | 76.5 |
| No Enzyme, 6000 psi | None | | 6000 psi | 72.3 |
| 0.3% sample | 0.3% Quest cocktail | pH 4 | 6000 psi | 5.2 |
| 0.3% sample | 0.3% Quest cocktail | pH 4.5 | 6000 psi | 8.3 |
| 0.3% sample | 0.3% Quest cocktail | pH 5 | 6000 psi | 8.6 |
| 1.5% sample | 1.5% Quest cocktail | pH 4 | 6000 psi | 3.8 |
| 1.5% sample | 1.5% Quest cocktail | pH 4.5 | 6000 psi | 4.9 |
| 1.5% sample | 1.5% Quest cocktail | pH 5 | 6000 psi | 4.3 |
| 3.0% sample | 3% Quest cocktail | pH 4 | 6000 psi | 3.3 |
| 3.0% sample | 3% Quest cocktail | pH 4.5 | 6000 psi | 3.2 |
| 3.0% sample | 3% Quest cocktail | pH 5 | 6000 psi | 5.3 |

The results of this Example showed that even at levels of enzyme as low as 0.3% of each enzyme, the amount of fat extraction from the cells was at a significant level, and at this level pH 4 was somewhat better than pH 4.5 or 5. At higher cocktail levels of 1.5% and 3% there was also good fat removal but the pH effect was not noticeable.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for obtaining a polyunsaturated fatty acid-containing lipid from a biomass, comprising:
   a) contacting an enzyme and a surfactant with a biomass at a temperature of about 10 degree Celsius to about 80 degree Celsius, and at a pH level of about pH 5 to about pH 9, said enzyme degrading a portion of the biomass impeding recovery of the lipid, and the portion of the biomass is selected from the group consisting of proteins, polysaccharides, cell wall, outer cell membrane, peptidoglycan layer, lipid bilayer, cellulose, chitin, hemicellulose, lignin, and lignin-related compounds,
   b) recovering said lipid having an anisidine value of 0.8 comprising at least 20 weight percent docosahexaenoic acid, at least 5 weight percent docosapentaenoic acid, and/or at least 20 weight percent arachidonic acid; and
   c) treating the recovered lipid by refining, bleaching, or deodorizing.

2. The method of claim 1, wherein the method is conducted in the substantial absence of an extraction solvent.

3. The method of claim 2, wherein said contacting is conducted at a temperature of about 40° C. to about 65° C.

4. The method of claim 1, wherein the biomass comprises a marine microorganism selected from the group consisting of algae, bacteria, fungi and protists.

5. The method of claim 1, wherein the biomass comprises an algae.

6. The method of claim 1, wherein the biomass comprises a microorganism selected from the group consisting of dinoflagellates and golden algae.

7. The method of claim 1, wherein the biomass comprises a microorganism selected from the group consisting of the genus *Thraustochytrium*, genus *Schizochytrium*, genus *Althornia*, genus *Aplanochytrium*, genus *Japonochytrium*, genus *Labyrinthula*, and genus *Labyrithuloides*.

8. The method of claim 1, wherein the biomass comprises a marine microorganism *Crypthecodinium cohnii*.

9. The method of claim 1, wherein the biomass comprises a marine microorganism genus *Schizochytrium*.

10. The method of claim 1, wherein the biomass comprises a fungus *Mortierella alpina*.

11. The method of claim 1, wherein said enzyme is selected from the group consisting of a lipase, a protease, a carbohydrase, a cellulase, a hemicellulase, a xylanthase, and a combination thereof.

12. The method of claim 1, wherein said contacting the biomass with an enzyme comprises treating said biomass with an enzyme cocktail comprising a protease, a carbohydrase, and a cellulase.

13. The method of claim 1, wherein said biomass is obtained by separating the biomass from a fermentation broth.

14. The method of claim 1, wherein said recovered lipid is in the form of an emulsion.

15. The method of claim 14, wherein the emulsion is treated by drying the emulsion to release the lipid from the emulsion.

16. The method of claim 1, further comprising treating said recovered lipid by at least one additional treatment selected from the group consisting of treatment with a polar organic solvent, salt, precipitating agent, a second enzyme, heating, and cooling.

17. The method of claim 1, wherein the recovered lipid is further treated by a treatment selected from the group consisting of drying, fractionating, winterizing, and interesterifying.

18. The method of claim 17, further comprising a treatment selected from the group consisting of treatment with antioxidants and metal ion capturing agents selected from the group consisting of chelating agents, ion exchange resins, and precipitating agents.

19. The method of claim 1, further comprising pressure disruption of the biomass.

20. The method of claim 19, wherein said pressure disruption comprises subjecting said biomass to a pressure differential of between about 2,000 psi and about 12,000 psi.

21. The method of claim 19, wherein said pressure disruption comprises subjecting said biomass to a pressure differential of between about 4,000 psi and about 10,000 psi.

22. The method of claim 19, wherein said pressure disruption comprises subjecting said biomass to a pressure differential of between about 5,000 psi and about 8,000 psi.

23. The method of claim 19, wherein said pressure disruption comprises subjecting said biomass to a pressure differential between about 6,000 psi and about 7,000 psi.

24. The method of claim 1, wherein the recovery of said lipid from the biomass is greater than about 90%.

25. The method of claim 1, wherein the recovery of said lipid from the biomass is greater than about 95%.

26. The method of claim 1, wherein at least a portion of said polyunsaturated fatty acid present in said lipid is a long chain polyunsaturated fatty acid.

27. The method of claim 1, wherein at least a portion of said polyunsaturated fatty acid present in said lipid has a carbon chain length of at least 20.

28. The method of claim 1, wherein at least a portion of said polyunsaturated fatty acid present in said lipid has a carbon chain length of at least 22.

29. The method of claim 1, wherein at least a portion of said polyunsaturated fatty acid present in said lipid has at least 3 double bonds.

30. The method of claim 1, wherein at least a portion of said polyunsaturated fatty acid present in said lipid has at least 4 double bonds.

31. The method of claim 1, wherein said polyunsaturated fatty acid comprises at least 30 weight percent docosahexaenoic acid.

32. The method of claim 1, wherein said polyunsaturated fatty acid comprises at least 10 weight percent docosapentaenoic acid.

33. The method of claim 1, wherein said polyunsaturated fatty acid comprises at least 15 weight percent docosapentaenoic acid.

34. The method of claim 1, wherein said polyunsaturated fatty acid comprises at least 20 weight percent docosapentaenoic acid.

35. The method of claim 1, wherein said polyunsaturated fatty acid comprises at least 30 weight percent arachidonic acid.

36. The method of claim 1, wherein said polyunsaturated fatty acid comprises at least 40 weight percent arachidonic acid.

37. The method of claim 1, wherein said polyunsaturated fatty acid comprises at least 50 weight percent arachidonic acid.

38. The method of claim 1, wherein said lipid comprises a monoacylglycerol.

39. The method of claim 1, wherein said lipid comprises a diacylglycerol.

40. The method of claim 1, wherein said lipid comprises a triacylglycerol.

* * * * *